(12) United States Patent
Gibertini

(10) Patent No.: US 7,538,116 B2
(45) Date of Patent: May 26, 2009

(54) TREATMENT OF SEXUAL DISORDERS

(76) Inventor: Michael Gibertini, 8- Edinburgh Dr., Randolph, NJ (US) 07869

(*) Notice: Subject to any disclaimer, the term of this patent is extended or adjusted under 35 U.S.C. 154(b) by 275 days.

(21) Appl. No.: 10/581,259

(22) PCT Filed: Dec. 1, 2004

(86) PCT No.: PCT/US2004/040116

§ 371 (c)(1),
(2), (4) Date: Jun. 1, 2006

(87) PCT Pub. No.: WO2005/053697

PCT Pub. Date: Jun. 16, 2005

(65) Prior Publication Data

US 2007/0123536 A1    May 31, 2007

Related U.S. Application Data

(60) Provisional application No. 60/526,365, filed on Dec. 1, 2003.

(51) Int. Cl.
*A61K 31/515* (2006.01)

(52) U.S. Cl. .................................... 514/275

(58) Field of Classification Search ................. 514/275
See application file for complete search history.

(56) References Cited

U.S. PATENT DOCUMENTS 4,640,921 A * 2/1987 Othmer et al. ......... 514/252.15

5,545,755 A * 8/1996 Lin et al. ..................... 564/428

FOREIGN PATENT DOCUMENTS

| WO | 02 41883 | 5/2002 |
| WO | 2004 045509 | 6/2004 |
| WO | 2005 007166 | 1/2005 |

OTHER PUBLICATIONS

Medelson, Scott D. et al., "Effects of 5-HT (1A) Selective Anxiolytics on Lordosis Behavior: Interactions with Progesterone", European Journal of Pharmacology, vol. 132, No. 2-3, pp. 323-326, 1986.
Gorzalka, Boris B. et al., "Serotonin Receptor Subtypes and Sexual Behavior" Annals of the New York Academy of Sciences, vol. 600, No. 0077-8923, pp. 435-446, 1990.
Rehman, Jamil et al., "Modification of Sexual Behavior of Long-Evans Male Rats by Drugs Acting on the 5-HT 1A Receptor", Brain Research, vol. 821, No. 0006-8993, pp. 414-425, 1999.
Choi, N. G. et al., "Modification of Sexual Behavior of Male Rats by Drugs Acting on Serotonin Receptor", Journal of Urology, vol. 139, pp. 253 A, 1988.
Murphy, Dennis L., "Neuropsychiatric Disorder and the Multiple Human Brain Serotonin Receptor Subtypes and Subsystem", Neuropsychopharmachology, vol. 3, No. 5/6, pp. 457-471, 1990.
Ennis, Michael D., "The Search for 5-HT1A Antagonists", Current Opinion in Therapeutic Patents vol. 3, No. 9, pp. 1325-1333, 1993.

* cited by examiner

*Primary Examiner*—San-ming Hui
(74) *Attorney, Agent, or Firm*—Oblon, Spivak, McClelland, Maier & Neustadt, P.C.

(57) ABSTRACT

The present invention relates to a method of treatment of sexual dysfunction e.g. female sexual disfunction by administering to a person in need of treatment an effective amount of gepirone as either a short-term or a long-term therapy.

11 Claims, No Drawings

TREATMENT OF SEXUAL DISORDERS

There is an increasing recognition that sexual disorders are responsive to medicinal treatment. The present invention focuses on a beneficial effect of a drug on sexual dysfunction, in particular on (hypoactive) sexual desire disorder, orgasmic disorder and sexual arousal disorder.

It is hard to extract from pre-clinical literature any reliable recommendation for use of drugs for certain sexual disorders, in particular if it concerns female sexual disorders. See, for example Rehman et al (Brain Research; vol 821; 1999; pp 414-425) in which the complex pharmacology of sexual responses in male animals is discussed with some excursions towards the human situation.

During the investigations of the anti-depressant effect of gepirone it was observed that formerly depressed patients appear to improve on sexual functioning upon resolution of the depression. In these same investigations, it was observed that gepirone-treated patients who remain depressed also had improvement in sexual functioning relative to those treated with placebo.

Thus, it has now been found that gepirone can be used with great benefit for the improvement of sexual drive and the treatment of a sexual dysfunction, in particular desire and arousal disorders, by administration of an effective amount of the drug as either a short-term or a long-term therapy.

In WO 02/41883, a method for treating premature ejaculation is disclosed, comprising administering to a male individual in need of such treatment, on an as-needed basis, a therapeutically effective amount of an antidepressant drug selected from the group consisting of tricyclic antidepressants, tetracyclic antidepressants, monoamine oxidase inhibitors, azapirone antidepressants, and atypical non-SRI antidepressants. Amongst numerous other possible active agents, also gepirone in suggested. Data are only presented for clomipramine hydrochloride, a tricyclic antidepressant. For the desired effect, a fast-acting pharmaceutical formulation is needed for the treatment on as-needed basis.

In contrast, as opposed to the immediate effect necessary in the treatment on as-needed basis, the present invention relates to the longer term (either short-term or long-term, even chronic) therapy for the treatment of sexual disorders in general.

Sexual disorders can occur as side effect in a treatment with an antidepressant with serotonin reuptake inhibiting effect. It is a specific embodiment of the invention to use gepirone for correcting such antidepressant-induced sexual side effects. Sexual disorders can also be observed as a prominent feature of the syndrome of depression. It is a specific embodiment of the invention to use gepirone for correcting such depression-related sexual problems. Finally, sexual disorders may occur spontaneously or for unknown reasons. It is a specific embodiment of the invention to use gepirone for correcting such primary sexual disorders in both men and women.

Treatment of sexual dysfunction in women can be effective with particular distinguishable effects in premenopausal women, in naturally menopausal women, in surgically menopausal women, in women taking hormone-containing products for hormone replacement therapy and in women taking hormone-containing products for contraception.

Definition of Terms:

There is renewed and recent discussion of diagnostic classification of female sexual disorders. In view of the movement in this area the description of this invention may have features characteristic of contemporary views on the disorders, whereas such views may evolve and make chosen terminology less clear. Nevertheless, independent of particular diagnostic labels, it is made available by this disclosure that the treatment with gepirone can be beneficial to a substantial group of patients having sexual disorder and experiencing the benefit of the drug's effects on sexual functioning. Those effects are improvement of libido and/or facilitation of reaching satisfactory orgasm and/or sexual intercourse. It should be understood that the described effect can be obtained as a group effect, whereby it must be accepted that some individuals in a group do not respond to the drug and that the effect of the invention can on those and other occasions be obtained recognizably in an individual person.

The diagnostic statistical manual, DSM-IV-TR, published by the American Psychiatric Association, provides a contemporary guideline for definition of the diagnostic category of sexual disorders unambiguously. In addition, the American Foundation of Urologic Diseases has published a similar guideline for such definition. The table below lists the major diagnoses in both classifications. It is clear that the diagnostic categories in both systems are commensurate and the specific embodiments for this invention are relevant to diagnoses made within either system.

| Diagnostic and Statistical Manual of Mental Disorders, Fourth Edition (DSM-IV) | American Foundation of Urologic Disease (AFUD) |
| --- | --- |
| Hypoactive sexual desire (302.71) | I. Sexual desire disorders: |
| Sexual aversion (302.79) |    A. Hypoactive sexual desire disorder |
| Female arousal disorder (302.72) |    B. Sexual aversion disorder |
| Female orgasmic disorder (302.73) | II. Sexual arousal disorder |
| Dyspareunia (302.76) | III. Orgasmic disorder |
| Vaginismus (306.51) | IV. Sexual pain disorders: |
|  |    A. Dyspareunia |
|  |    B. Vaginismus |
|  |    C. Other sexual pain disorders |

The population group aimed for as in need of treatment with gepirone, according to the present invention is a group of human persons, male or female, for which a sexual dysfunction is causing marked distress or interpersonal difficulties. If the sexual dysfunction is a minor or secondary part of the group of commonly observed symptoms characteristic for major or atypical depression, anxiety, panic disorder, drug abuse or any other diagnostic category for which it is known to use gepirone as treatment and the sexual dysfunction is not at the forefront of the complaints to the extent that it is a major reason to need treatment for the patient, it is not the type of sexual dysfunction for which gepirone is the indicated treatment according to this invention. When gepirone is used as a general antidepressant, it may be expected that any depression-related symptom, such as sexual dysfunction, will wane off upon treatment of depression or anxiety or any of the other diseases mentioned above, as part of the beneficial effect of gepirone on such diseases. However, it is the unexpected finding of this invention that a sexual dysfunction, which is at the forefront of the complaints of a patient can be beneficially treated by gepirone administration, independent of the anti-depressant, anti-anxiety, anti-drug abuse or anti-panic effect of gepirone.

Specific categories of sexual disorders for treatment with gepirone, with reference to the numbered categories in DSM IV, are:

302.71 Hypoactive Sexual Desire Disorder: Persistently or recurrently deficient (or absent) sexual fantasies and desire for sexual activity.

302.72 Female Sexual Arousal Disorder: Persistent or recurrent inability to attain, or to maintain until completion of the sexual activity, an adequate lubrication-swelling response of sexual excitement.

302.73 Female Orgasmic Disorder: Persistent or recurrent delay in, or absence of, orgasm following a normal sexual excitement phase.

302.74 Male Orgasmic Disorder: Persistent or recurrent delay in, or absence of, orgasm following a normal sexual excitement phase.

302.79 Sexual Aversion Disorder: Persistent or recurrent extreme aversion to, and avoidance of, all, or almost all genital sexual contact with a sexual partner.

302.76 Dyspareunia in a female, not due to a general medical condition: Recurrent or persistent genital pain associated with sexual intercourse in a female.

306.51 Vaginismus (not due to a general medical condition: Recurrent or persistent involuntary spasm of the musculature of the outer third of the vagina that interferes with sexual intercourse.

302.72 Male erectile disorder: Persistent or recurrent inability to attain, or to maintain until completion of the sexual activity, an adequate erection.

A preferred embodiment is the treatment of (hypoactive) sexual desire disorder, female sexual arousal disorder and male and female orgasmic disorder. Treatment of sexual desire disorder is a more preferred embodiment, in particular of female sexual desire disorder.

The Derogatis Interview for Sexual Functioning (DISF/DISF-SR) is a specific example of a method to diagnose sexual dysfunctions, but other methods are also available, see:

Derogatis LR; The Derogatis Interview for Sexual Functioning (DISF/DISF-SR): An Introductory Report. Journal of Sex & Marital Therapy. Vol. 23(4) (pp 291-304), 1997; Derogatis L R. Laban M P: Psychological assessment measures of human sexual functioning in clinical trials. International Journal of Impotence Research. Vol.10 (SUPPL. 2) (pp S13-S20), 1998. Meston C M. Derogatis L R: Validated instruments for assessing female sexual function. Journal of Sex & Marital Therapy. Vol. 28 (SUPPL. 1) (pp 155-164), 2002. These and other methods can be used to apply the treatment to selected patient groups.

The term gepirone is used here as the non-proprietary name of 4,4-dimethyl-1-[4-[4-(2-pyrimidinyl)-1-piperazinyl]butyl]-2,6-piperidinedione. It commonly refers to the chemical compound as a base, but, depending on the context, may also refer to the a salt and solvate thereof. The HCl salt is most commonly in use.

While it is possible to administer gepirone, or a pharmaceutical acceptable acid addition salt or solvate thereof, alone it is preferable to present it as a pharmaceutical composition adapted for the treatment of sexual disorders, comprising gepirone, or a pharmaceutically acceptable acid addition salt or solvate thereof, mixed with one or more pharmaceutically acceptable auxiliaries.

The medicament comprising gepirone may be administered enterally (e.g. orally, rectal nasal or topically) or parenterally (e.g. via intramuscular, subcutaneous, intravenous or intraperitoneal injections).

It is a specific embodiment of the invention to use gepirone for the manufacture of a medicine for the treatment of sexual dysfunction, in particular the mentioned specific diagnostic categories.

A unit treatment dose (=a dosing unit) is an amount of gepirone in a pharmaceutical presentation form for administration to a subject at a particular point in time. A daily treatment dose can be administered in one or more dosage units suitable for example for the oral, the rectal, the sublingual or the nasal route or through the skin (for example, transdermal patches, or in the form of a cream). An effective amount for treatment will be a daily amount of administration in the range of from 1 to 120 mg gepirone (base or HCl salt) and can be selected for optimal effect based on type of disorder, duration of desired drug effect, tolerance to the receiving patient, gender, age and physical condition of the patient. A needed daily amount can be administered in several dosage units, but it is preferred to administer the dose in a single daily treatment dose or in a formulation releasing gepirone chronically in the required amount per day. Dose units for once-a-day treatment containing the mentioned amount of from 1 to 120 mg can be used for, for example, oral administration. Tablets containing 15, 30, 40, 60 and 80 mg of gepirone are specific examples of suitable oral dose units. Of course, any amount within these ranges can be selected. A daily treatment amount in the range of from 15 to 80 mg and corresponding once-a-day oral dose units for treatment of sexual disorders will be a specific embodiment of the invention.

The invention further includes a patient pack for treatment of sexual disorders comprising dose units in combination with packaging material suitable for said dose units, whereby the dose units comprise pharmaceutical auxiliaries and gepirone in a suitable amount between 1 and 120 mg and optionally, said packaging material is including means to help a recipient using the dose units most suitably for the treatment of a sexual disorder. Such means to help a recipient using the dose units most suitably for the treatment as described herein before are, for example, instructions for the use of the composition. In such a patient pack the intended use of a formulation comprising gepirone for the treatment of sexual disorders can be inferred by instructions, facilities, provisions, adaptations and/or other means to help using the formulation most suitably for the treatment. Such measures make a patient pack specifically suitable for and adapted for use for treatment of a sexual disorder.

For making means of dosing, such as pills, tablets, suppositories, (micro-)capsules, powders, emulsions, creams, ointments, implants, a patch, a gel, and any other preparation for sustained release, sprays, injection preparations in the form of a solution or suspension, suitable auxiliaries such as carriers, fillers, binders, lubricants, dispersants, emulsifiers, stabilisers, surfactants, anti-oxidants, colorants, preservatives and the like can be used e.g. as described in the standard reference, Gennaro et al., Remington; The Science and Practice of Pharmacy; 20th ed., Publisher: Lippincott Williams & Wilkins; Baltimore; USA in Part 5) and the Handbook of Pharmaceutical Excipients (3nd edition edited by Arthur H. Kibbe; Published by the American Pharmaceutical Association, Washington D.C. and The Pharmaceutical Press, London in 2000). In general any pharmaceutically acceptable auxiliary which does not interfere with the function of the active compound is suitable and can be used.

Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts.

Binders are agents used to impart cohesive properties to a pharmaceutical composition resulting in minimal loss from the pharmaceutical composition during production and handling. Binders are for example cellulose, starches, polyvinylpyrrolidone, and the like.

A suitable lubricant with which the active agent of the invention can be administered is, for example, magnesium stearate.

Surfactants are agents facilitating the contact and migration of compounds in different physical environments such as hydrophilic and hydrophobic environments. Many surfactants are known in the art of making pharmaceutical compositions as for example described in chapter 21 of Gennaro et al, Remington; The Science and Practice of Pharmacy; 20th ed., Publisher: Lippincott Williams & Wilkins; Baltimore; USA). Surfactants that can be used during the process of preparing the pharmaceutical formulation are, for example, polyethylene glycol (PEG), and the like.

Specifically useful for pharmaceutical formulations of gepironeHCl are tablets having a matrix consisting of a cellulose ether in an amount selected in the range of from 55% to 85 wt % of total tablet mass and a carbohydrate binder of, for example, cellulose (7 to 10 wt % microcrystalline cellulose, such as Avicel pH 101), sugars, starches, amylopectin, dextrin, maltodextrin, gums and alginates.

Suitable cellulose ethers can be used for these tablets as carrier in dry-mix tablets, as binder in wet-granulation and can be used in coating techniques as film-forming polymers. Such carriers tend to retain in aqueous environment other ingredients for a longer time upon absorption of water in the outer layer and consequently are suitable for extended release formulation. Examples of such carriers can be found in the group of hydroxy-(1C-3C)alkyl(1C-3C)alkylcelluloses, such as hydroxymethylcellulose, hydroxyethylcellulose and the preferred hydroxypropylmethylcellulose (HPMC). Other gel-forming carriers can be found in the standard compilation of pharmaceutically acceptable carriers and excipients, the Handbook of Pharmaceutical Excipients (3nd edition edited by Arthur H. Kibbe; Published by the American Pharmaceutical Association, Washington D.C. and The Pharmaceutical Press, London in 2000). Specific reference is made, for incorporation into this specification, to the extended release formulations described in U.S. Pat. No. 5,478,572. In particular, extended release formulations are suitable for the treatment according to the present invention.

Gepirone may be prepared using the method described in U.S. Pat. No. 4,423,049 which method is incorporated herein by reference.

EXAMPLES

Sexual dysfunction and recovery were measured with the Derogatis Interview for Sexual Functioning (DISF/DISF-SR). This provides for a coordinated set of brief matched instruments designed to provide an estimate of the quality of an individual's current sexual functioning. The DISF is a semi-structured interview comprising 25 items and reflecting quality of sexual functioning in a multi-domain format. The DISF-SR is a matching Self-Report (SR) inventory designed to accomplish the same goal in a patient self-report mode. There are gender specific male and female versions of both the DISF and the DISF-SR. All instruments in the DISF series are designed to be interpreted at three distinct levels: Discrete Items, Functional Domains, and aggregate summary (Total Score). The Discrete Items are arranged into five primary Functional Domains of sexual functioning: (I) sexual cognition/fantasy, (II) sexual arousal, (III) sexual behavior/experience, (IV) orgasm, and (V) sexual drive/relationship. Both the DISF and the DISF-SR take approximately 12 to 15 minutes to administer. Internal consistency reliabilities for domain scores of the DISF-SR range from 0.70 to 0.77, while test-retest stability coefficients are 0.80 to 0.90 and 0.86 for the Total Score. Inter-rater reliability estimates for the DISF interview ranged from 0.84 to 0.92 for domain scores, and 0.91 for the Total. The DISF/DISF-SR has demonstrated good discriminative validity and sensitivity to treatment-induced changes in both male and female versions, and gender-keyed actuarial norms (in terms of area T-scores) are available for all versions of the instrument. The DISF/DISF-SR is currently available in 10 foreign languages.

Procedure:

The Derogatis Interview was used, providing information on the quality of the subject's sexual functioning in quantitative terms. Only subjects who were willing to discuss their sexual functioning with the investigator were to be included. In addition, the scores from the interview, as well as demographic and medical history information, were to be used by the investigator to determine whether or not the subject reached the threshold of disorder (absent or present) for the primary criteria for the DSM-IV Sexual Disorders.

Effects of Short-term Treatment (2 Months)

DISF-SR data from the combined analysis of two investigations of gepirone in depressed outpatients (Organon internal reference: 134001 and 134002) were analyzed. For females in these investigations, data were available for 79 subjects who received gepirone and 77 subjects who received placebo. The mean change from baseline in total score was +8.0 with a SD of 26.8 for those subjects who received gepirone, compared with +4.0 with a SD of 21.7 for those subjects who received placebo. For males, data were available for 37 subjects who received gepirone and 49 subjects who received placebo. The mean change from baseline in total score was +13.7 with a SD of 25.2 for those subjects who received gepirone, compared with −0.6 with a SD of 19.3 for those subjects who received placebo. When comparing the mean change from baseline in total score only, these results suggest an improvement in sexual functioning for both females and males who received gepirone, when compared with subjects who received placebo. Upon analysis of mean change from baseline in scores for each DISF-SR domain, a similar interpretation of the results could be made.

DISF interview data from the analysis of another investigation of gepirone in depression (Organon internal reference number: 134004) were analyzed. For females, data were available for 75 subjects who received gepirone, 84 subjects who received fluoxetine, and 85 subjects who received placebo. The mean change from baseline in total score was +4.3 with a SD of 26.5 for those subjects who received gepirone, compared with −3.5 with a SD of 24.4 for those subjects who received fluoxetine and +0.4 with a SD of 21.8 for those subjects who received placebo. For males, data were available for 45 subjects who received gepirone, 47 subjects who received fluoxetine, and 42 subjects who received placebo. The mean change from baseline in total score was 0 with a SD of 22.5 for those subjects who received gepirone, compared with −4.4 with a SD of 30.4 for those subjects who received fluoxetine and +1.9 with a SD of 17.9 for those subjects who received placebo. When comparing the mean change from baseline in total score only, these results suggest an improvement in sexual functioning for females who received gepirone when compared with subjects who received fluoxetine or placebo. For males, the results suggest that there is no change in sexual functioning for subjects who received gepirone. For both females and males who received fluoxetine, the mean change from baseline in total score suggests a worsening of sexual functioning, a known effect of this drug. Upon analysis of change from baseline in total score only for each domain for females and Domains I to III for males, similar conclusions for subjects who received gepirone and fluoxetine could be drawn. Analysis of the change from baseline in total score only for Domains IV (orgasm) and V (sexual drive/relationship) for males suggested that there was an improvement in total score from baseline for those subjects who received gepirone.

Effects of Longer-term Treatment (Greater Than 2 Months)

In a trial on antidepressant effect and with further assessment of effects on sexual functioning with gepirone (Organon's internal reference number 28709) subjects were exposed to gepirone HCl (40 mg in extended release [ER] formulation) for 8 to 12 weeks in order to obtain remission from the current episode of depression. After remission, subjects were randomized to receive either gepirone HCl ER or placebo. For females, data were available for 57 subjects who received gepirone and 49 subjects who received placebo. The mean change from baseline in total score was +5.2 with a SD of 33 for those subjects who received gepirone, compared with +8.1 with a SD of 26.8 for those subjects who received placebo. For males, data were available for 27 subjects who received gepirone and 31 subjects who received placebo. The mean change from baseline in total score was +18.7 with a SD of 25.9 for those subjects who received gepirone, compared with +3.4 with a SD of 25.1 for those subjects who received placebo. When comparing the mean change from baseline in total score only, these results suggest an improvement in sexual functioning for both genders, regardless of treatment group. However, for males treatment with gepirone seems to have a better effect on sexual functioning when compared to placebo. Upon analysis of each domain for females and Domains I to III for males, similar conclusions could be drawn. Analysis of Domains IV (orgasm) and V (sexual drive/relationship) for males suggested that there was an improvement in total score from baseline for subjects who received gepirone.

In this study the patients are no longer depressed. The fact that DISF scores continue to increase in those subjects for many months, long after the depression is over, illustrates that gepirone can be stimulatory of sexual function.

In another study (Organon's Internal reference number 134501), all subjects received gepirone ER (40 mg) after having completed a trial wherein subjects were randomized to receive either gepirone ER or placebo. DISF-SR data from the analysis of this long-term trial were analyzed. For females, data were available for 23 subjects who received gepirone in a previous trial (Organon internal reference: 134001 or 134002) previously (henceforth referred to as gepirone in this paragraph) and 23 subjects who received placebo previously (henceforth referred to as placebo in this paragraph). The mean change from baseline in total score was +11.2 with a SD of 29.9 for subjects who received gepirone, compared with +3.3 with a SD of 24.8 for subjects who had received placebo. For males, data were available for 17 subjects who received gepirone and 17 subjects who received placebo. The mean change from baseline in total score was +12.3 with a SD of 30.6 for subjects who received gepirone, compared with −4.4 with a SD of 20.5 for subjects who received placebo. The results seem to indicate that for both females and males, extended treatment with gepirone (i.e. beyond 8 weeks) has a positive effect on sexual function. Upon analysis of each domain, this interpretation seems to be consistent for both genders for Domains I to III and V. For males, the interpretation seems to be consistent for Domain IV and for females, it seems that there is no difference in effect on the total score between the two groups of subjects. DISF Interview data from the analysis of another long-term trial (Organon internal reference: 134502) were analyzed. In this trial subjects from a previous trial (Organon internal reference:134004) were continued on therapy or were switched to a new drug, depending on antidepressant response. For females, data were available for 14 subjects who received gepirone in both the short-term (Organon internal reference:134004) and long-term (Organon internal reference:134502) trials, 24 subjects who received fluoxetine throughout, and 29 subjects who received placebo throughout. The mean change from baseline in total score was +18.1 with a SD of 38.3 for those subjects who received gepirone, compared with +12.8 with a SD of 22.4 for those subjects who received fluoxetine and +1.6 with a SD of 26.7 for those subjects who received placebo. Data for females were also available for 36 subjects who switched from fluoxetine in the short-term trial to gepirone in the long-term trial, 24 subjects who switched from placebo to gepirone, and 24 subjects who switched from gepirone to fluoxetine. The mean change from baseline in total score was +2.3 with a SD of 18.6 for those subjects who switched from fluoxetine to gepirone, +4.2 with a SD of 30 for those subjects who switched from placebo to gepirone, and +0.9 with a SD of 28.5 for those subjects who switched from gepirone to fluoxetine. For males, data were available for 14 subjects who received gepirone throughout, 14 subjects who received fluoxetine throughout, and 8 subjects who received placebo throughout. The mean change from baseline in total score was +5.5 with a SD of 31.9 for those subjects who received gepirone, compared with −1.2 with a SD of 27.2 for those subjects who received fluoxetine and +3.3 with a SD of 40.1 for those subjects who received placebo. Data for males were also available for 18 subjects who switched from fluoxetine to gepirone, 18 subjects who switched from placebo to gepirone, and 19 subjects who switched from gepirone to fluoxetine. The mean change from baseline in total score was +3.3 with a SD of 13.2 for those subjects who switched from fluoxetine to gepirone, +7.1 with a SD of 16.1 for those subjects who switched from placebo to gepirone, and −5.8 with a SD of 22.4 for those subjects who switched from gepirone to fluoxetine. The mean change from baseline total scores for females who continued with the same treatment seem to indicate that there is some improvement in sexual functioning for subjects who received gepirone when compared with subjects who received fluoxetine or placebo. Upon analysis of the mean change from baseline in total score for each domain, similar results were found.

For males, the mean change from baseline in total score seems to indicate that extended treatment (i.e. over 8 weeks) with gepirone improves sexual functioning when compared to the scores for subjects who received extended treatment with fluoxetine or placebo. Upon analysis of the mean change from baseline in total score for each domain, there was not a clear difference between gepirone or the fluoxetine or placebo groups. For both females and males who switched treatment, the mean change from baseline in total score seems to indicate that switching to gepirone had a beneficial effect on sexual functioning when compared to switching to fluoxetine. Upon analysis of the mean change from baseline in total score for each domain, there was not a clear difference between subjects who switched to gepirone and subjects who switched to fluoxetine, regardless of the gender.

Specific Case Descriptions

In another trial patients were enrolled in a long-term open-label study of depressed patients. During the trial, subjects had spontaneously reported that their sexual desire and function had dramatically improved during the course of therapy. It was observed that most of the reports were from patients in long-term therapy who had recovered from their depression weeks to months before making the reports. These reports provided incidental observations on both men and women of various ages that sexual desire had increased to a level not previously experienced by the subject and which was quite pleasing to them. It appeared that these patients were no longer depressed and now had the added benefit that sexual function, sexual relationships, and quality of life were improved beyond that experienced by patients merely recovering from depression.

It was found that a man in his 50's who had been on gepirone for nearly a year had reported that his libido was up and had been up for many weeks. He was pursuing a dating life for the first time in years. Another observation was of a lesbian woman on open-label therapy who had for the first time in her life begun experiencing "rolling orgasms" which were both more frequent and more intense than she had known. She was not depressed anymore and the sexual effects continued to increase.

It was found that a female patient in her late 30's who had been widowed for 3 years was suddenly taken with the urge to "find a man" and had begun using an internet dating service. She was successful and carried out a satisfying sexual relationship for the fist time since the death of her husband. She was reported to be "giddy" over the effects of gepirone in this domain. Her quality of life was judged as much improved by the investigator.

The invention claimed is:

1. A method of treatment of sexual dysfunction by administering to a person in need of treatment an effective amount of gepirone as either a short-term or a long-term therapy, wherein said sexual dysfunction is a sexual disorder selected from the group consisting of hypoactive sexual desire disorder, orgasmic disorder, and sexual arousal disorder.

2. The method of treatment according to claim 1, wherein the sexual dysfunction is orgasmic disorder.

3. The method of treatment according to claim 1, wherein the sexual dysfunction is hypoactive sexual desire disorder.

4. The method of treatment according to claim 1, wherein the sexual dysfunction is arousal disorder.

5. The method of treatment according to claim 1, wherein the sexual dysfunction is female sexual dysfunction.

6. The method of treatment according to claim 1, wherein the sexual dysfunction is male sexual dysfunction.

7. The method of treatment according to claim 1, wherein said person in need of treatment further suffers from major depression.

8. The method of treatment according to claim 1, wherein said person in need of treatment further suffers from atypical depression.

9. The method of treatment according to claim 1, wherein said person in need of treatment further suffers from anxiety.

10. The method of treatment according to claim 1, wherein said person in need of treatment further suffers from panic disorder.

11. The method of treatment according to claim 1, wherein said person in need of treatment further suffers from drug abuse.

* * * * *